US006363789B1

(12) United States Patent
Rassaian et al.

(10) Patent No.: US 6,363,789 B1
(45) Date of Patent: Apr. 2, 2002

(54) ACOUSTIC PRESSURE LOAD CONVERSION METHOD TO VIBRATION SPECTRA

(75) Inventors: Mostafa Rassaian, Bellevue; Jung-Chaun Lee, Federal Way; Gerould K. Young, Mercer Island; Alan Edqar Landmann, Bellevue, all of WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 09/584,646

(22) Filed: May 31, 2000

(51) Int. Cl.[7] .............................................. G06F 17/50
(52) U.S. Cl. ............................ 73/663; 73/849; 700/97; 700/98
(58) Field of Search .......................... 73/663, 662, 849, 73/850, 851, 852; 700/95, 97, 98, 103, 108, 109

(56) References Cited

U.S. PATENT DOCUMENTS

| 4,084,427 A | | 4/1978 | Jacoby et al. ................. 359/15 |
| 4,589,288 A | * | 5/1986 | Porter et al. .................. 73/852 |
| 4,894,787 A | | 1/1990 | Flannelly et al. ............. 702/42 |
| 4,955,269 A | | 9/1990 | Kendig et al. ................ 73/577 |
| 5,060,516 A | * | 10/1991 | Lau et al. ..................... 73/602 |
| 5,163,011 A | | 11/1992 | Gunsallus .................... 702/42 |
| 5,531,122 A | | 7/1996 | Chatham et al. .............. 73/760 |
| 5,815,394 A | * | 9/1998 | Adeli et al. .................. 700/97 |
| 5,930,155 A | | 7/1999 | Tohi et al. ..................... 703/8 |
| 6,053,052 A | * | 4/2000 | Starostovic .................. 73/851 |
| 6,090,147 A | * | 7/2000 | Bremner et al. ............... 703/1 |
| 6,926,329 | * | 7/2001 | Sikora et al. ................ 702/175 |

FOREIGN PATENT DOCUMENTS

| JP | 6-331506 | * | 12/1994 |
| JP | 11-230850 | * | 8/1999 |
| JP | 2000-293548 | * | 10/2000 |

* cited by examiner

Primary Examiner—Hezron Williams
Assistant Examiner—Rose M. Miller
(74) Attorney, Agent, or Firm—Harness Dickey & Pierce P.L.C.

(57) ABSTRACT

A method is provided for testing structural-acoustic systems using a shaker table. The method includes subjecting a panel structure design to a computational acoustic load and a computational vibration load. The method then computes the ratio of the panel structure maximum response to the acoustic load to the panel structure maximum response to the vibration load. The ratio of these two maximum responses provides a conversion factor for linking an acoustic environment to a vibration environment. Using the conversion factor, the method converts a sonic pressure load for the panel structure to a vibration load. The vibration load is then applied to a panel structure using a shaker table.

13 Claims, 9 Drawing Sheets

ACOUSTIC PRESSURE LOAD CONVERSION METHOD TO VIBRATION SPECTRA

TECHNICAL FIELD

This invention relates to sonic fatigue testing methods for panel structures, and more particularly to a method of testing the response of a panel structure to acoustic pressure by simulating the sonic load spectrum of the acoustic pressure with a vibration spectrum on a shaker table.

BACKGROUND OF THE INVENTION

Modern aircraft and missiles operate in environments wherein extreme acoustic pressures are common. The panel structures making up the aircraft must be able to withstand these extreme acoustic pressures. To ensure this ability, new panel structures for aircrafts are subjected to stringent acoustic testing.

Testing the response of a panel structure to acoustic pressure fluctuations, random both in time and space, essentially reduces to evaluating a dimensionless quantity known in the art as "joint acceptance". Joint acceptance corresponds to the coupling between the excitation pressure field and the structure. The joint acceptance function is defined by:

$$J_{jm}(\omega) = \frac{1}{A^2} \int_a \int_{a'} C(\underline{r}, \underline{r}', \omega) \phi_j(\underline{r}) \varphi_m(\underline{r}') da\, da'$$

$d\underline{a}, d\underline{a}'$=infinitesimal area vectors $C(\underline{r},\underline{r}', \omega)$=cross-power spectral density coefficient of the sound pressure field A=pressure surface area $\underline{r},\underline{r}'$=space vectors locating points on the structure The joint acceptance is computed by mapping the differential elements in integration space using the Jacobi method at the integrated degrees of freedom.

Displacement power spectral density response, $W_y(\underline{r}),\omega)$ is equal to:

$$W_y(\underline{r}, \omega) = \frac{A^2 G(\omega)}{\omega^4} \sum_j \sum_m \frac{\phi_j(\underline{r})\phi_m(\underline{r}) J_{jm}(\omega)}{M_j M_m |H_j(\omega)||H_m(\omega)|}$$

where $$H_j(\omega) = \left(-1 + 2\xi_j \frac{\omega_j}{\omega}\text{Im} + \frac{\omega_j^2}{\omega^2}\right)$$

$M_j$, $M_m$=$J^{th}$, and $m^{th}$ elements of generalized mass matrix $\phi_j(r)$=$j^{th}$ normal mode shape $|\cdot|$=amplitude of complex variable $G(\omega)$=reference power spectral density of sound pressure $J_{jm}(\omega)$=joint acceptance The root-mean-square displacement is given by $$u(\underline{r}) = \left(\int_{\omega_l}^{\omega_f} W_y(\underline{r}, \omega) d\omega\right)^{1/2}$$

Modal joint acceptance was first applied to a simply supported beam in *"On The Fatigue Failure Of Structure Due To Vibrations Excited By Random Pressure Fields"*, *Journal of Acoustical Society of America*, Volume 30, No. 12, December 1958, Pages 1130–1135. Subsequent development yielded a method to determine the modal joint acceptance of a flat or cylindrical panel structure with arbitrary boundary conditions with a homogeneous random pressure field. Predictive methods were also developed to quantify the random excitation of the structure due to boundary layer noise.

Ideal testing of joint acceptance involves the manufacturing of a full sized prototype and then placing the prototype in an acoustic chamber wherein the sonic load spectrum of the acoustic pressures at a typical operating environment is duplicated. The response of each panel structure of the prototype is then monitored. As can be appreciated, however, building prototypes and subsequent testing in an acoustic chamber is impractical on a large scale basis due to the extreme complexity, time consumption and expense.

To avoid the complexity and expense of such test environments, most new panel structures are tested for acoustic response through simulation and analysis. Numerous prior art computational methods have been developed over the years to compute the behavior of such structural-acoustic systems. These modeling approaches can be separated into three main methods:

1. The acoustic-boundary integral method;
2. Finite element modeling representing the acoustic-structural interaction method involving fluid; and
3. The statistical energy-analysis method.

Of the above approaches, finite element modeling has found particular usefulness in the aircraft industry.

Finite element modeling involves the creation of a computer model of a proposed panel structure. The computer model is then tested against certain design criteria for its suitability. If the computer model is deemed suitable, a prototype panel is built and tested for its response to acoustic pressure by exposing it to a sonic load spectrum.

Unfortunately, such testing still requires the prototype panel to be subjected to a sonic load spectrum. This was deemed necessary since the response of a panel structure to a sonic load spectrum depends in a complex way on its position relative to the source, the existence of intervening structure, and the orientation of the panel in space. A significant drawback of such testing is the complexity and expense of generating the sonic load spectrum.

In view of the foregoing, it would be desirable to provide a method for testing a panel structure which obviates the need for generating the sonic load spectrum. For example, it would be advantageous to simulate the sonic load spectrum with an equivalent vibration spectrum. Such a vibration spectrum could easily be generated by, for example, an inexpensive shaker table.

SUMMARY OF THE INVENTION

In preferred embodiments, the present invention is directed towards a method of testing structural-acoustic systems using an inexpensive shaker test. In particular, the preferred embodiment of the present invention provides advantages over prior art techniques including simplified sonic-fatigue qualification testing, a fully parametric environment integrating structural-acoustic methods for computing the vibro-acoustic behavior of a structure under random excitation, the ability to capture large and complex geometries with arbitrary boundary conditions, and to investigate structural response for non-linear and thermal load based residual stress problems.

In one preferred embodiment, the method includes subjecting a model of a panel structure to computational acoustic and vibration loads. The method then computes the ratio of the maximum responses of the panel structure model to the acoustic and vibration loads. The ratio of these two maximum responses provides a conversion factor for linking an acoustic environment to a vibration environment. Using the conversion factor, a sonic load spectrum for testing against the panel structure is converted to a vibration load. The vibration load can then be applied to the panel structure using a shaker table.

To determine the conversion factor, it is presently preferred to apply two computational loads to a model of the panel structure. The first computational load consists of a 1 psi uniform pressure representing an acoustic pressure having a magnitude accounted for following a mode-superposition method. The second computational load consists of a 1 g negative base acceleration representing a vibration load having a response generated by a mode-acceleration method for random vibration.

Ideally, pressure load boundary conditions consistent with the in situ structure conditions of the panel structure are also applied to the model. Also, acceleration load boundary conditions consistent with the pressure load boundary conditions are preferably applied to the model of the panel structure. After applying the two computational loads, methodology determines the maximum pressure response of the model to the computational acoustic pressure load and the maximum acceleration response of the model to the computational acceleration load. The conversion factor is the ratio of the pressure response maximum to the acceleration response maximum.

In another preferred embodiment of the present invention, the above-determined conversion factor is used in sonic fatigue qualification testing of a panel structure. In this embodiment, the sonic pressure level that the panel structure is to be tested against is initially defined. The sonic pressure level is then converted to a pressure power spectral density using conventional techniques. The pressure power spectral density is then converted to an acceleration power spectral density using the conversion factor described above. The acceleration power spectral density is then used to generate input for a shaker table. The panel structure is then placed on the shaker table and monitored for its response to the input.

BRIEF DESCRIPTION OF THE DRAWINGS

The various advantages of the present invention will become apparent to one skilled in the art by reading the following specification and subjoined claims and by referencing the following drawings in which:

FIG. 9 is a flowchart depicting a method of performing a sonic fatigue qualification test on a panel structure using a shaker table for generating vibration input with the conversion link of the present invention.

DETAILED DESCRIPTION OF THE PREFERRED EMBODIMENTS

The present invention is directed towards a method of determining a conversion factor for linking an acoustic environment to a vibration environment. The conversion factor enables base-acceleration random input to be substituted for acoustic pressure excitation in panel structure testing. Such a substitution will find particular usefulness in performing sonic fatigue testing of a panel wherein an inexpensive shaker test can be employed rather than a conventional and costly acoustic test.

Figure 1:
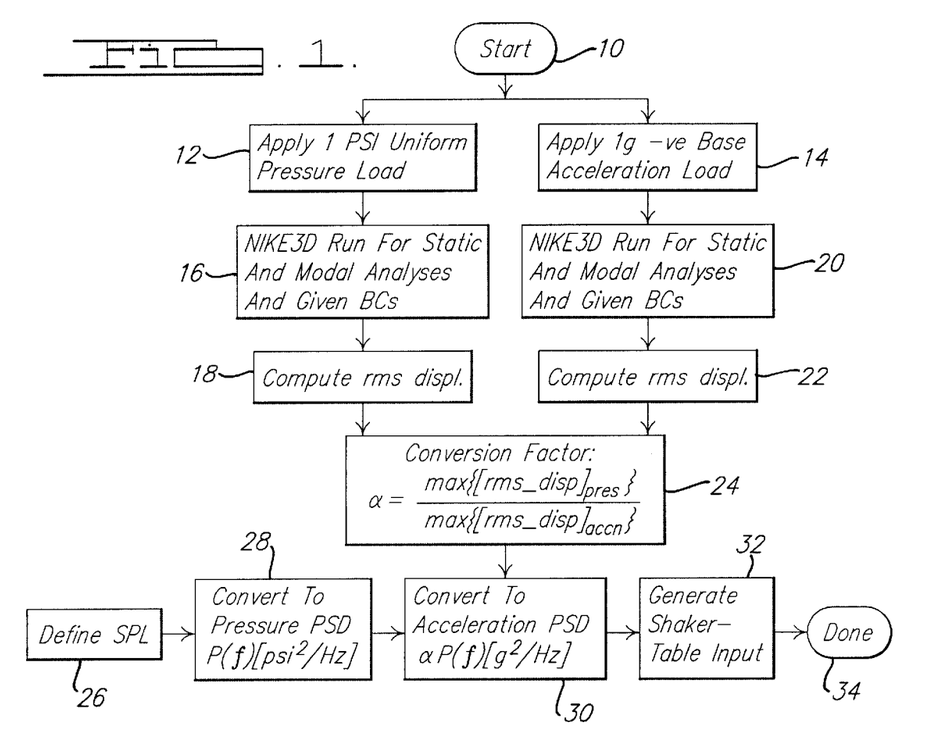
FIG. 1 is a flowchart depicting a method of determining a conversion factor for linking an acoustic environment to a vibration environment, and the use of the conversion factor in vibration testing.

Referring now to FIG. 1, the methodology of the present invention is illustrated. The methodology begins at bubble 10 and falls through to blocks 12 and 14. In block 12, a computational acoustic wave having a uniform pressure load is applied to a model of a panel structure. More particularly, a 1 psi pressure load is applied to the model as a means to map a given acoustic pressure. Preferably, the methodology utilizes a known mode-superposition method for accounting for the magnitude of the acoustic pressure load. After applying the acoustic pressure load at block 12, the methodology advances to block 16.

In block 16, pressure load boundary conditions consistent with the in situ structural mount conditions of the panel structure are applied to the model. Such boundary conditions may include, for example, the fasteners holding the panel structure to a conventional test assembly. From block 16, the methodology continues to block 18 which includes both static and modal analyses. In block 18, the methodology determines the root mean square displacement response of the model to the applied unit pressure power spectral density and boundary conditions.

Referring again to block 14, the methodology also applies a computational vibration load to the model of the panel structure. The vibration load preferably is in the form of an acceleration load. More particularly, a 1 g negative base-acceleration load is applied to the model as a necessary lead case toward random vibration analysis. Preferably, the methodology utilizes a known mode-acceleration method for generating the acceleration load as random vibration to achieve numerical performance. After applying the acceleration load at block 14, the methodology continues to block 20 which includes both static and modal analyses. In block 20, acceleration load boundary conditions which are equal to the pressure-load boundary conditions described above are applied to the model.

From block 20, the methodology continues to block 22. In block 22, the methodology determines the root mean square displacement response of the model to the applied acceleration power spectral density load and base-excitation boundary conditions. From blocks 18 and 22, the methodology continues to block 24. In block 24, the methodology determines the ratio of the peak root means square displacement responses of the panel structure as computed in blocks 18 and 22.

More particularly, in block 24, the methodology determines the ratio of the maximum response of the panel structure model to the pressure power spectral density load to the maximum response of the panel structure model to the acceleration power spectral density load. This ratio is a scalar which is independent of space and frequency. As such, the ratio can be used as a conversion factor for converting an acoustic environment to a vibration environment and vice versa.

Once the conversion factor has been computed in block 24, a vibration test can be employed for simulating an acoustic pressure test. In block 26, the methodology defines the sound pressure level (i.e., the sonic load spectrum) that the panel structure is to be tested against. Typically, this will be input from a designer. After defining the sound pressure level at block 26, the methodology continues to block 28.

In block 28, the sound pressure level is converted to a pressure level power spectral density. This is preferably accomplished using conventional techniques such as one-third-octave sound pressure level via:

$$G(f) = 8.41 \times 10^{(SPL/10)-18}/0.2310 f_c;$$

wherein $f_c$ is the center frequency.

After converting the sound pressure level to a pressure level power spectral density in block 28, the methodology continues to block 30.

In block 30, the pressure level power spectral density is converted to an acceleration level power spectral density. This conversion is made by applying the conversion factor determined at block 24 to the pressure load power spectral density determined at block 28. More particularly, the pressure level power spectral density is multiplied by the conversion factor to yield the acceleration level power spectral density. If desired, the inversion of the conversion factor may be used to convert an acceleration level power spectral density to a pressure level power spectral density. After determining the acceleration level power spectral density at block 30, the methodology continues to block 32.

In block 32, the methodology employs the acceleration level power spectral density determined at block 30 as an input for a shaker-table. The panel structure can then be placed on the shaker table and monitored for its response to the input. After applying the shaker-table input at block 32, the methodology continues to bubble 34 where it exits the process pending a subsequent execution thereof.

It should be noted that the general method of relating an acoustic input to a vibration input has been illustrated as implemented in a NIKE3D system in a dual path but can be equally implemented to other systems. Further, the method utilizes mode-superposition for acoustic pressure and mode-acceleration for random vibration. Note that mode-acceleration does not constitute the joint acceptance function. As such, mode-acceleration cannot be employed in a straightforward manner for solving acoustic problems. However, the mode-superposition method can be used to simulate both acoustic pressure and acceleration spectral-density generalized forces. The use of mode-acceleration is preferred for vibration analysis to enable an improved convergence and a shorter computing time compared to mode-superposition.

Figure 2:
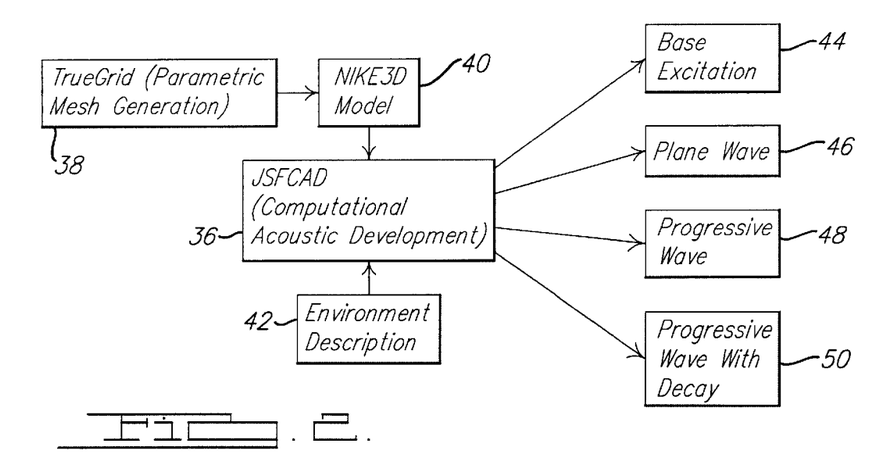
FIG. 2 is a flowchart depicting a method of converting an acoustic or vibration environment into the other environment using a parameterization feature of the present invention.

Turning pow to FIG. 2, the methodology of the present invention is illustrated in a parametric form. In the illustrated embodiment, the method of FIG. 1 for determining the conversion link between the acoustic environment and the vibration environment is employed at block 36.

Referring now to block 38, the methodology initially constructs a finite-element model of a panel structure to be tested such as, for example, a new aircraft panel design. Preferably, a TrueGrid system or other 3D solid or shell element meshing system is used in a parametric form for constructing the finite element model. As one skilled in the art will appreciate, these models would initially be derived with a CAD design from the designer. After the methodology generates a finite element model at block 38, the methodology continues to block 40.

In block 40, the methodology performs optimization computations on the baseline finite-element model generated at block 38. Preferably, this is accomplished using the NIKE3D system or an equivalent thereof. After constructing the finite element model at block 40, the methodology continues to block 36.

In block 36, the methodology applies a pre-selected environmental description (e.g., an acoustic pressure load or an acceleration load) from block 42 to the finite element model from block 40. The environmental description is preferably provided by a designer to correspond to a given test criteria. The methodology then converts the input environment condition from block 42 to another environment, applies the load to the model, and determines the stress response of the model. For example, if the environment description from block 42 describes an acoustic pressure load, the methodology in block 36 converts it to a base excitation as shown in block 44, applies the acoustic pressure load to the model, and determines a stress response due to the acoustic load.

On the other hand, if the environmental description at block 42 describes an acceleration load, the methodology at block 36 converts it to an acoustic pressure load, applies the base-excitation acceleration load to the model, and determines a stress response due to the acceleration load. If desired, the stress response can be determined for an acoustic pressure load in the form of a plane wave as shown at block 46, a progressive wave as shown at block 48, or a progressive wave with decay as shown in block 50. Preferably, this is accomplished by setting a flag in the environment description file in block 42.

Figure 3:
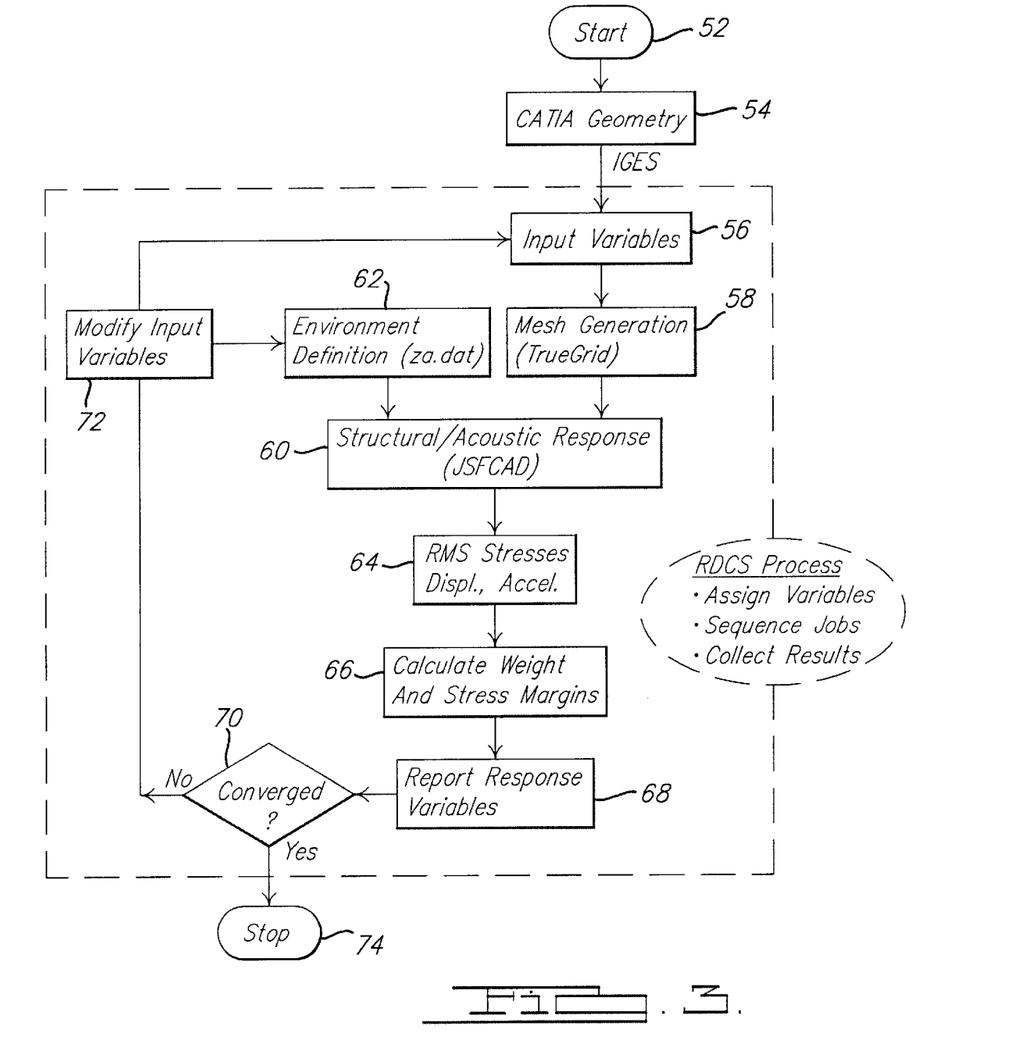
FIG. 3 is a flowchart depicting a method of optimizing a panel structure design for weight and stress tolerance using the methodology of the present invention.

Turning now to FIG. 3, the methodology of the present invention for converting between an acoustic environment and a vibration environment is illustrated in a Robust Design Computational System for performing optimization computations on a panel structure. In the illustrated embodiment, the methodology is depicted for optimizing weight and stress tolerance of a new design panel in a parametric fashion. Of course, other design criteria could substitute for those described.

The methodology starts in bubble 52 and continues to block 54. In block 54, the methodology obtains the geometric description of the panel to be tested. Typically, a designer would initially create the proposed panel design using a system such as CATIA and then input the design geometry into the methodology. After obtaining the design geometry at block 54, the methodology continues to block 56.

In block 56, the methodology obtains a plurality of input variables for the panel design. These variables may include for example, ranges of panel size and wall thicknesses initially set by the designer. When optimizing the design, the methodology adjusts these variables within pre-selected constraints to optimize the panel design. After defining the input variables at block 56, the methodology continues to block 58.

In block 58, the methodology generates a parametric finite-element model of the panel design based on the geometry from block 54 and the variables from block 56. Preferably, a TrueGrid or similar 3D solid or shell meshing system is employed to create the finite element model. After creating the finite element model at block 58, the methodology advances to block 60.

In block 60, the methodology applies the method of FIG. 1 to determine the structural responses of the model generated at block 58 against an environment definition provided from block 62. The environment definition from block 62 may be, for example, an acoustic pressure load or an acceleration load. The environment definition is initially set by the designer and preferably corresponds to a given test criteria. The structural responses of the model are determined for pre-selected points along the model and may include, for example, displacement and/or acceleration among others depending on the environment definition from block 62.

After determining the structural responses of the model to the load at block 60, the methodology continues to block 64. In block 64, the methodology determines the root mean square of the structural responses determined at block 60. After determining the root mean square of the structural responses at block 64, the methodology continues to block 66.

In block 66, the methodology determines the nature of the pre-selected design features to be optimized based on the structural responses. In the illustrated embodiment, the pre-selected design features to be optimized include weight and stress margins in view of the prescribed ranges of panel size and wall thickness from block 56. After determining the weight and stress margins at block 66, the methodology continues to block 68.

In block 68, the methodology reports the values of a set of response variables from the test to a checking portion of the program. The response variables, such as panel thickness, must be within certain constraints for the new design to be deemed acceptable. If the response variables are outside of the limits, the checking portion of the program reruns or skips the test of the given set of input conditions. If the response variables are within the specified limits at block 68, the methodology continues to decision block 70.

In decision block 70, the methodology determines whether the model is optimized by determining if the weight and stress margins are within certain pre-selected limits. This should also include the solution convergence of a study case. These limits, or conversion constraints, are based on parameters that indicate changes in the objective function of the panel design from one iteration of the methodology to the next. If the margins are outside of the pre-selected limits at decision block 70, the panel design is not yet optimized. As such, the methodology advances from decision block 70 to block 72.

In block 72, the methodology modifies the value of the input variables within the pre-set ranges. After modifying the input variables at block 72, the methodology continues to block 56. In block 56, the modified input variables are used to create an updated model for use during the next run. The methodology also advances from block 72 to block 62 so that the environment definition can also be modified as part of the input conditions for the next run, if desired.

Referring again to decision block 70, if the margins for the panel design are within the pre-selected limits, the panel design is deemed optimized. As such, the methodology advances from decision block 70 to bubble 74 and exits the analytic process pending a subsequent execution thereof. It should be noted that a preferred environment for employing the methodology depicted in FIG. 3 is a distributed queuing system. The results of the methodology preferably include sensitivity analysis of the root mean square displacement, acceleration, or stress response in terms of each input variable. This results in an optimum design for meeting a set of performance criteria, while optimizing the weight in a minimal amount of time.

Figure 4A:
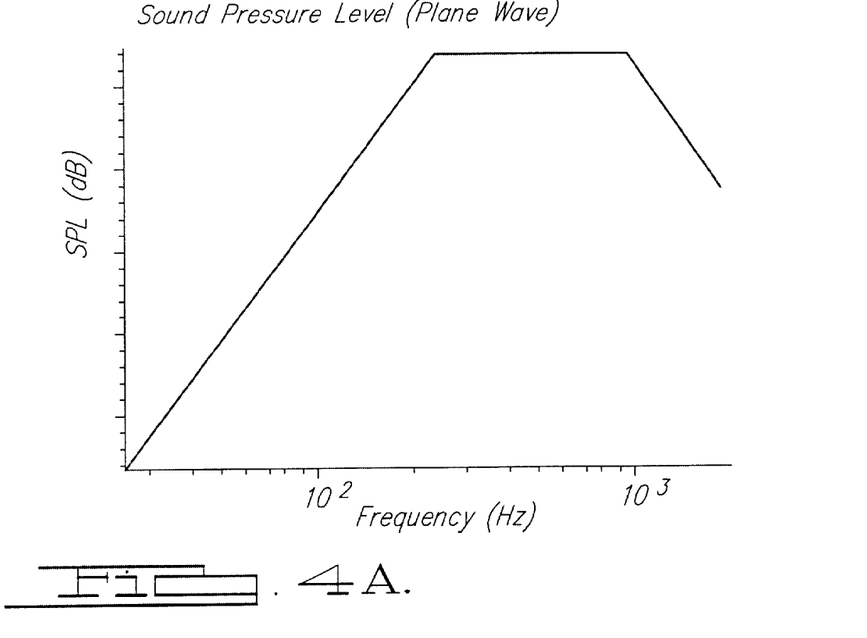
FIGS. 4A and 4B are graphic illustrations depicting panel structure response to sound pressure level and its equivalent, computationally derived, acceleration power spectral density relative to changes in frequency.
Figure 4B:
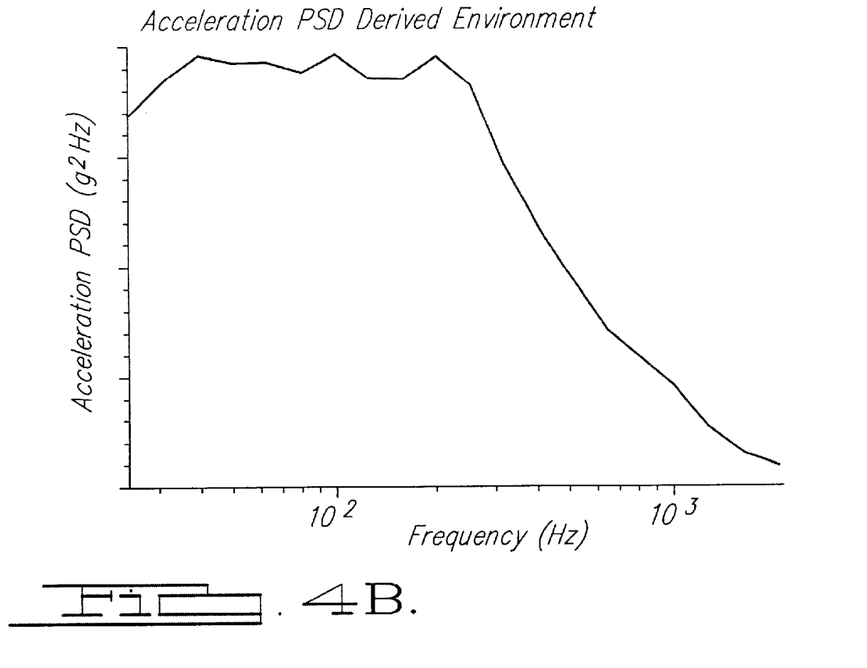

Turning now to FIGS. 4a and 4b, the methodology of the present invention was validated by subjecting a 2-sheet titanium panel to plane-wave flow excitation. More particularly, a pressure power spectral density for the panel was calculated based on a pre-selected sound pressure level. The resulting pressure power spectral density was applied to the 2-sheet titanium panel finite-element model as a plane wave pressure field excitation. The sound pressure level versus frequency results are illustrated in FIG. 4a. A conversion factor was then determined using the methodology illustrated in FIG. 1 and a predicted base-acceleration power spectral density was determined. The acceleration power spectral density versus frequency prediction is illustrated in FIG. 4b.

Figure 5A:
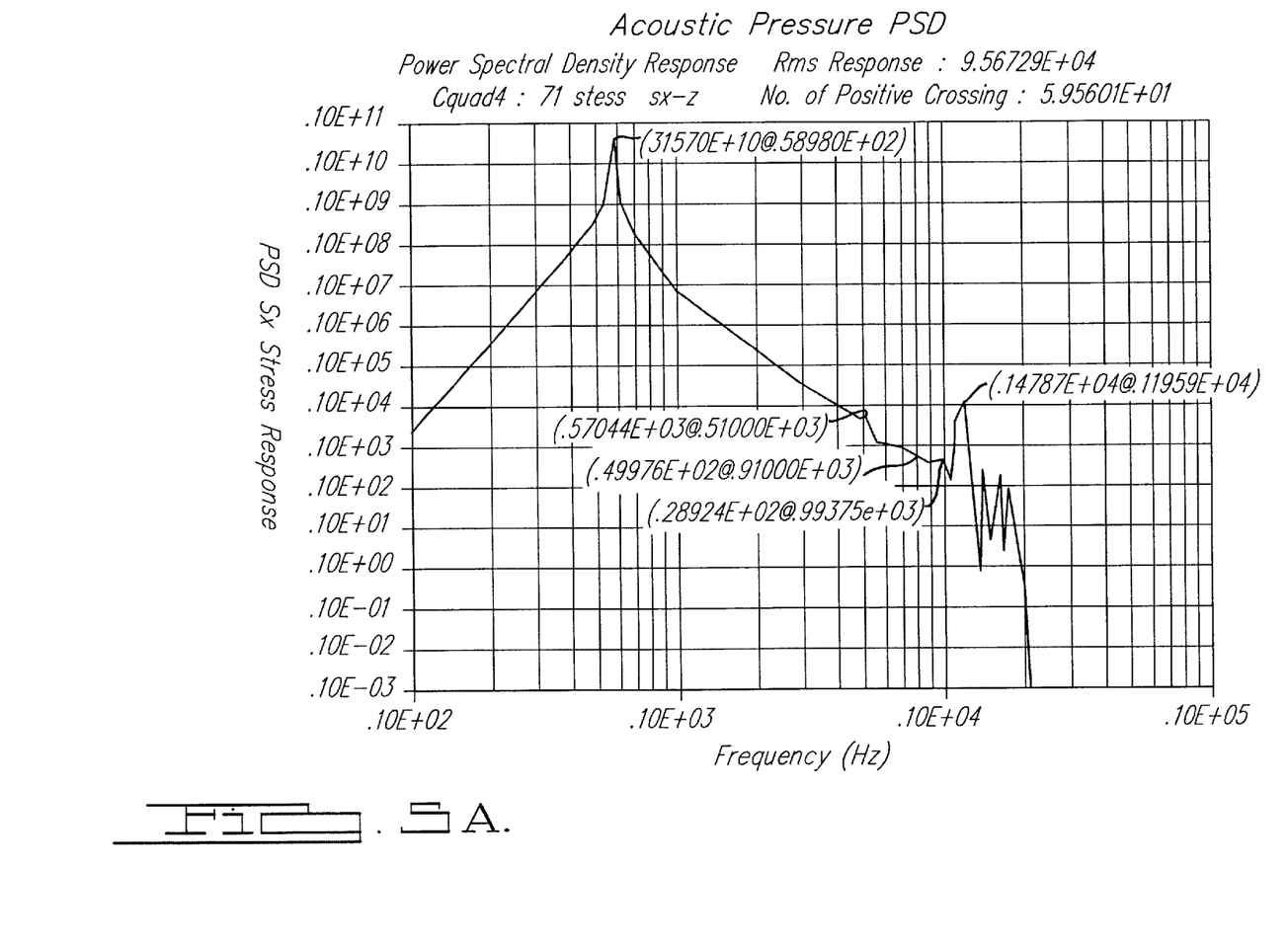
FIGS. 5A and 5B are graphic illustrations depicting panel structure response to acoustic pressure power spectral density and its equivalent, computationally derived, base acceleration power spectral density relative to changes in frequency.
Figure 5B:
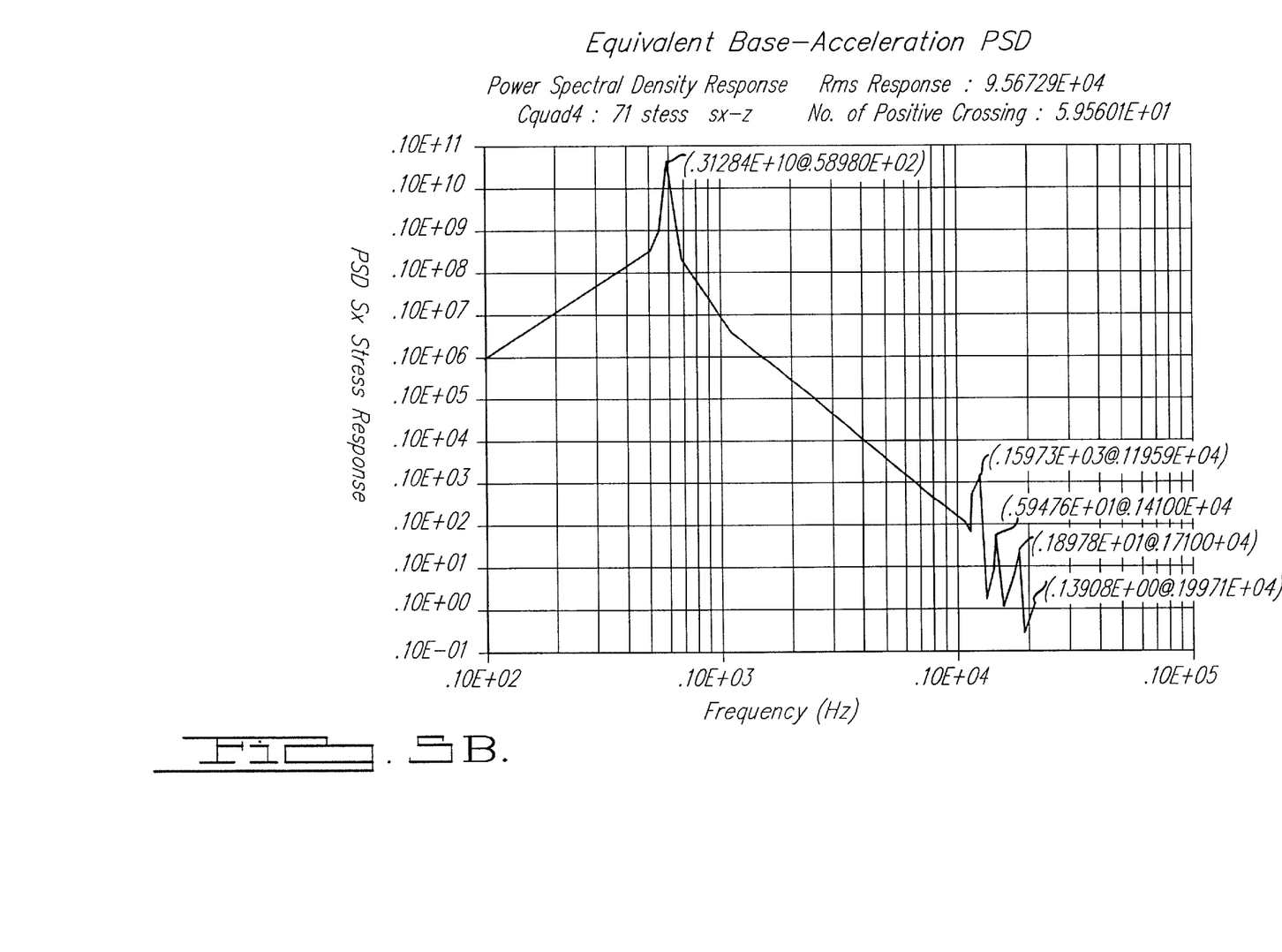

Turning now to FIGS. 5a and 5b, the accuracy of the conversion link of the present invention was verified by comparing a finite-element analysis of the panel response to the pressure power spectral density and base-acceleration power spectral density. FIGS. 5a and 5b illustrate the results of the two models comparing their respective tensile stress spectral density response functions. The results show that the fundamental frequency at 60 Hz matches the test results and the fundamental mode of vibration dominates the panel structure response by orders of magnitude.

It should be noted that the analysis which generated the results illustrated in FIGS. 5a and 5b was carried out using 3 percent uniform modal damping based on 25 modal responses. The resultant distribution of root mean square Von Mises stress values due to acoustic pressure and its equivalent vibration load is identical. This demonstrates the accuracy of the present methodology for a realistic panel structure. The peak power spectral density, stress response, is found near the fixed edge of this panel structure. The results at the fundamental frequency are also identical, indicating that the local Power Spectral Densities match precisely.

Figure 6:
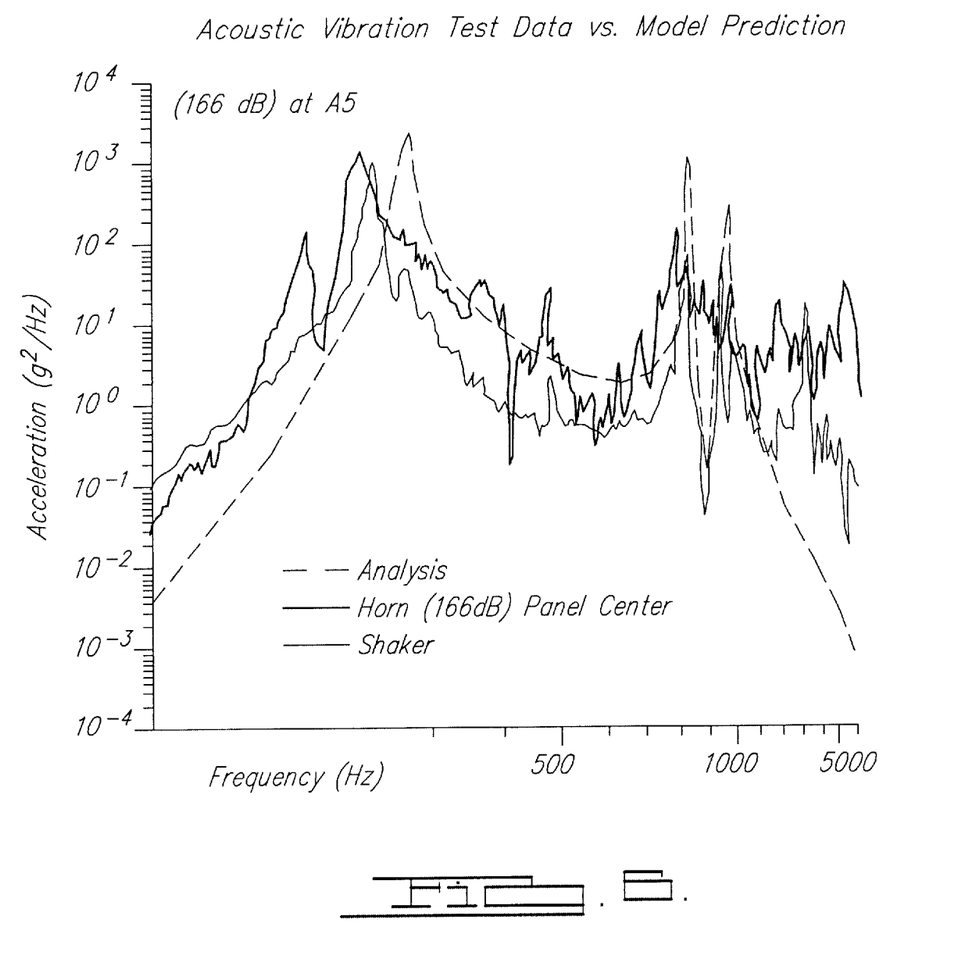
FIG. 6 is a graphic illustration depicting panel structure response to acoustic and vibration test data, and the analysis method verifying the pressure and base acceleration relative to changes in frequency.

Referring now to FIG. 6, a comparison between model and physical measurements of a test panel is illustrated. For this purpose, a 4-sheet Titanium panel was exposed to three sound pressure levels of 150, 158, and 166 dB in an acoustic chamber. By applying the analytical conversion link of the present invention, the derived equivalent base-excitation acceleration levels were used to define shaker-table input. The acceleration power and spectral-density functions measured at various points on the panel are different in shape and magnitude, and vary with the position on the panel.

The plot illustrated in FIG. 6 shows a relative comparison of the test results as predicted by the analysis. The response represents the acceleration power spectral density corresponding to 166 dB at a point centrally located on the 4-sheet Titanium panel. As observed, the results are strikingly similar in both magnitude and broad frequency content, proving the accuracy of the developed analytical conversion link experimentally. The analysis-method validation by testing represents an instrumental milestone that was successfully accomplished by the present invention.

It should also be noted that a sonic and vibration test program was designed to validate the present analytical approach for linking a sonic pressure field to a vibration-acceleration environment. In addition, the accuracy of the high-cycle fatigue method as a part of an overall sonic qualification process was confirmed. To accomplish this, the panel was initially subjected to the stress condition associated with the plane wave for a fatigue test. This was generated by a traditional Miles equation predicting failure at much lower levels.

Figure 7A:
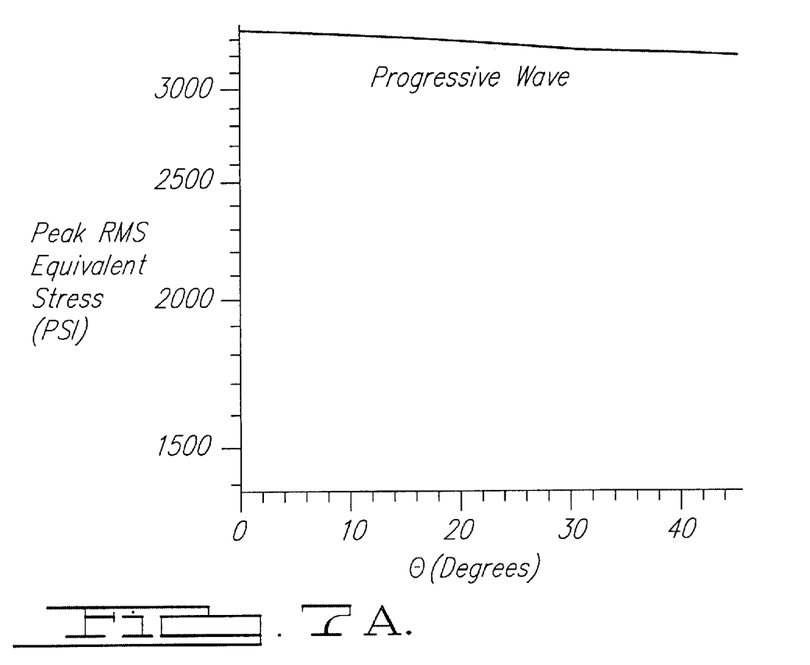
FIGS. 7A and 7B are graphic illustrations depicting peak root mean square equivalent stress and peak root mean square deflection of a panel structure relative to changes in panel inclination angle to the direction of convection.
Figure 7B:
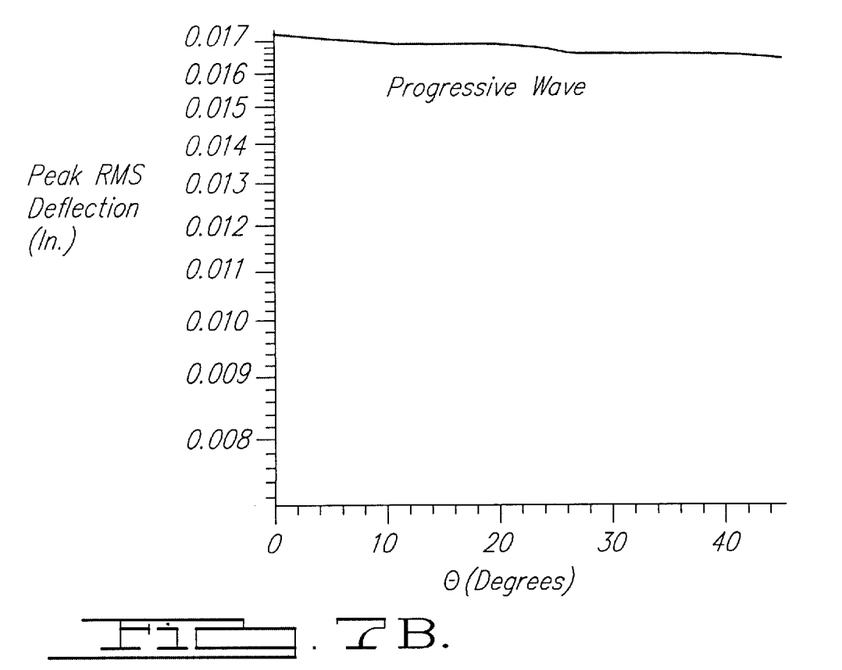

Referring now to FIGS. 7a and 7b, a parametric study was conducted to determine the effect of flow angle and coherence degradation to high-cycle fatigue damage. In FIGS. 7a and 7b, the sensitivity of orientation angle to the panel characteristic response was investigated for a 4-sheet titanium panel. This study was done for progressive-wave excitation when the panel inclination to the direction of convection is varied between 0 and 45 degrees. The peak root means square Von Mises stress and deflection responses are shown in FIGS. 7a and 7b. The results indicate that the variation of structural response to the flow angle for the progressive pressure field is fairly small.

Figure 8A:
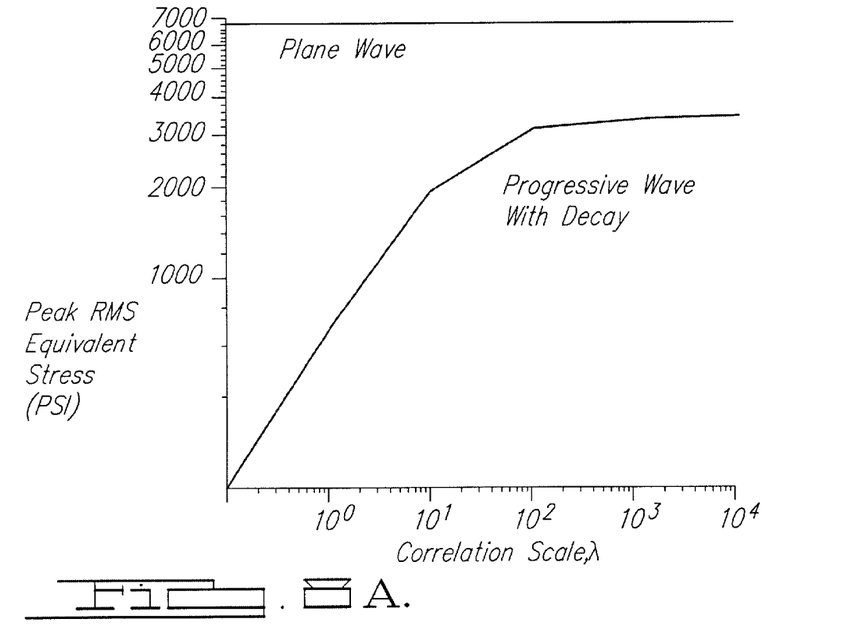
FIGS. 8A and 8B are graphic illustrations depicting peak root mean square equivalent stress and peak root mean square deflection of a panel structure subjected to a plane wave pressure field and a progressive wave pressure field with decay relative to a correlation scale.
Figure 8B:
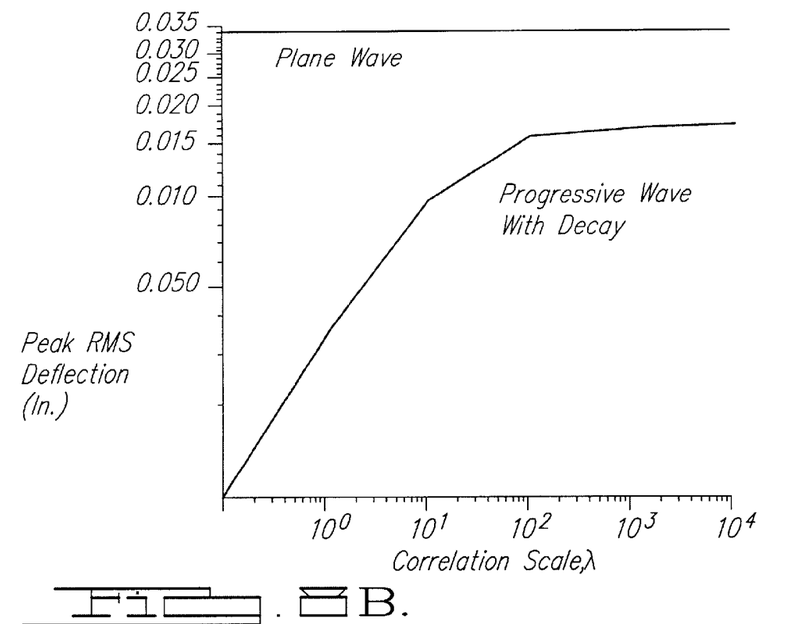
Figure 10:
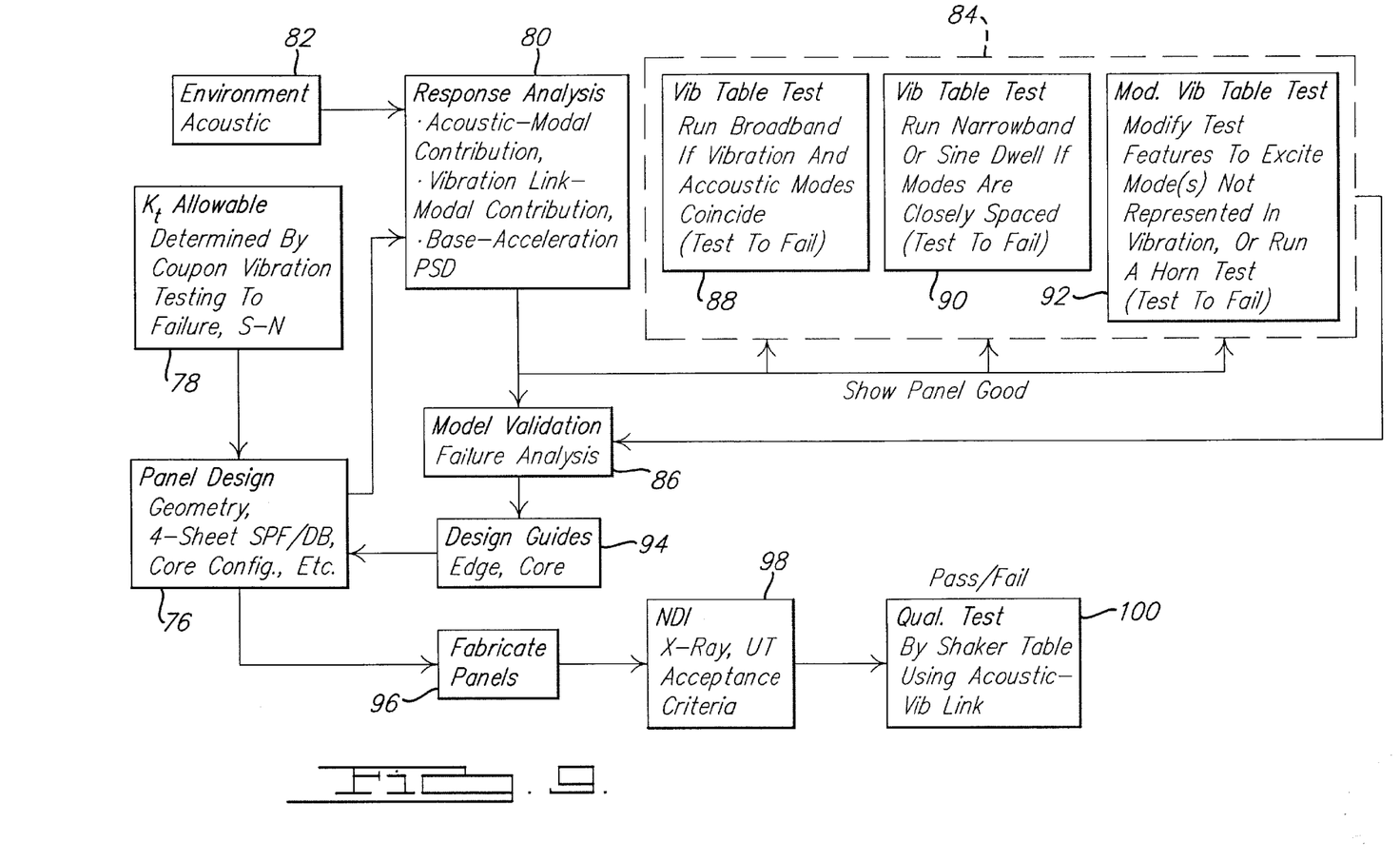

Referring to FIGS. 8a and 8b, a parametric study was also conducted to determine the effect of correlated, partially correlated, and uncorrelated load to high-cycle fatigue damage. In FIGS. 8a and 8b, sensitivity analysis was performed to determine the impact of a plane wave and a progressive wave to a 4-sheet titanium panel. The main concern focuses upon the type of pressure field which best represents a real acoustic environment governing the response of the panel structure. This is a fundamental step in design and in response prediction for a structure immersed in an acoustic field.

The results in FIGS. 8a and 8b are shown for peak root mean square Von Mises stress as well as peak displacement response. As expected, the plane wave is fully correlated, thus the response remains independent of the correlation scale. The results also indicate that the progressive wave with decay is monotonically increased by the correlation scale and approaches the response, due to a progressive wave without decay, asymptotically. Considering that the plane wave is assumed in conventional methods, the results demonstrate the degree of conservatism this assumption introduces in panel design.

Referring now to FIG. 9, an overview of a design and analysis qualification process using the methodology of the present invention will now be described. As a foundation for a life assessment of a panel structure from acoustic stimulation, the developed prediction method relies on coupon-level fatigue data. Developing the analytical model of the system is essentially a two-step process. In the first step, a shaker test is performed on the coupon after a design is identified. In the second step, the stress concentration factor is computed by detail finite-element analysis.

The essence of the first step is to individually excite modes of failure by carefully designed loading conditions in the test setups. The vibration input generated by the analytical link represents a given acoustic environment to replicate on the shaker table. The recorded fatigue behavior, by means of the measured strain versus frequency of load application combined with the computed stress concentration factor, is then used to establish life expectancy. Understanding the failure mechanisms in this process will also help improve the design and track the stress margins.

Extra care is required if dominant structural modes under noise cannot be reproduced by basic acceleration. This is the case for panels with closely spaced but distinct modes. In this situation, the computed vibration spectrum should be compensated if the derived analytical factor, due to absent modes in vibration simulation, is significant.

The final step involves the qualification test to the acoustic excitation at the component level. It encompasses non-flat complex structures with mechanisms that can be characterized on a shaker table and meet the design expectations. This is accomplished by using the methodologies described above on the shaker table with anticipated modes of failure and life expectancy. This process provides a significant cost savings, particularly during the non-destructive qualification testing, attributable to simplified procedure.

Still referring to FIG. 9, an exemplary qualification testing method is illustrated. With reference to block 76, the methodology initially obtains a panel design having certain geometrical singularities characterized by $K_t$ from block 78. From block 76, the methodology continues to block 80. In block 80, the response of the panel is analyzed for a spatial correlation function characterized by generic surface acoustics from block 82. In this case, the acoustic environment in block 82 represents a noise environment from model jet impingement test data.

From block 80, the methodology continues to blocks 84 and 86. In block 84, the analytical link is deployed to evaluate the damage contribution on the panel due to both acoustic pressure and its equivalent base-acceleration. In block 86, the analysis results guide a meaningful test that may involve multiple panels with multiple modes to show the panels are appropriate for a type of testing. For example, a broad band random vibration test at block 88 is appropriate if the panel response due to acoustic pressure is captured by the base acceleration. A narrow band or sine dwell at block 90 is appropriate is there are a number of modes present that are closely spaced. A modified vibration table test at block 92 is appropriate if the respective analysis show significantly different modal participation factors. Note, however, that the sequence of testing at block 84 leading to model validation at block 86 is optional.

From the model validation at block 86, the methodology continues to block 94. In block 94, design guides are developed to enhance panel design at block 76. Once the optimum panel design is determined, the methodology advances from block 76 to block 96. In block 96, prototype panels are fabricated according to the design.

From block 96, the methodology continues to block 98. In block 98, the prototype panels are inspected. From block 98, the methodology continues to block 100. In block 100, the inspected panels are tested on a shaker table using the conversion factor to generate random vibration input corresponding to the desired acoustic pressure load. The integrity of the design is demonstrated by a pass/fail criterion.

In view of the foregoing, it can be appreciated that the present invention relates a general acoustic environment, such as a plane wave, progressive wave, reverberant pressure field, or a combination of these, to a base-excitation acceleration for evaluating the response of a panel on a shaker table. In this process, the peak stress response due to the acoustic and vibration fields are matched in order to extract a conversion factor. The methodology can also simulate the response of a panel to either a vibration or acoustic environment. The structural response obtained enables identification of the modal response and damage contribution. The analysis results produced assist in deciding the type of test to run and what modes to excite. For example, a sine dwell may be performed on the modes of vibration that contribute the most damage.

Those skilled in the art can now appreciate from the foregoing description that the broad teachings of the present invention can be implemented in a variety of forms. For example, while the conversion link of the present invention was developed in a NIKE3D environment, the formulation can also be implemented in a NASTRAN environment. Therefore, while this invention has been described in connection with particular examples thereof, the true scope of the invention should not be so limited since other modifications will become apparent to the skilled practitioner upon a study of the drawings, specification, and following claims.

What is claimed is:

1. A method of determining a link for relating a first environment to a second environment comprising:
    subjecting a panel structure model to a computational first load;
    subjecting the panel structure model to a computational second load;
    determining a maximum response of the panel structure model to the first load;
    determining a maximum response of the panel structure model to the second load; and
    determining a ratio of the maximum responses, said ratio being the link relating the first environment to the second environment.

2. The method of claim 1 wherein the panel structure model comprises a finite-element model of a panel structure and the method further comprises:
    obtaining a first environment load to test against the finite-element model;
    applying the ratio of the maximum response to the first environment load to convert the first environment load to a second environment load;
    subjecting the finite-element model to the second environment load; and
    determining a stress response of the finite-element model due to the second environment load.

3. The method of claim 2 wherein the first environment load further comprises one of an acoustic pressure load and an acceleration load and the second environment load further comprises the other of the acoustic pressure load and the acceleration load.

4. The method of claim 1 wherein the computational first load further comprises a 1 psi uniform pressure load.

5. The method of claim 1 wherein the computational second load further comprises a 1 g negative base acceleration load.

6. The method of claim 1 wherein the computational second load is generated by mode-acceleration.

7. The method of claim 1 further comprising applying pressure load boundary conditions to the panel structure model prior to determining the ratio of maximum responses.

8. The method of claim 1 further comprising applying acceleration load boundary conditions to the panel structure model prior to determining the ratio of maximum responses.

9. A method of testing a panel structure for sonic fatigue using a shaker table comprising:
    subjecting a model of the panel structure to a computational acoustic load;
    applying acoustic load boundary conditions to the model;
    determining a maximum pressure response of the model to the acoustic load and acoustic boundary conditions;
    subjecting the model to a computational acceleration load;
    applying acceleration load boundary conditions to the model;
    determining a maximum acceleration response of the model to the acceleration load and acceleration boundary conditions;
    determining a ratio of the maximum pressure response to the maximum acceleration response;
    selecting a sonic pressure load for testing against the panel structure;
    converting the sonic pressure load to a pressure power spectral density;
    applying the ratio of the maximum pressure response to the maximum acceleration response to the pressure power spectral density to convert the pressure power spectral density to an acceleration power spectral density;
    generating input for the shaker table according to the acceleration power spectral density;
    securing the panel structure to the shaker table;
    applying the input to the shaker table; and
    monitoring the response of the panel structure to the input.

10. The method of claim 9 wherein the acoustic load further comprises a 1 psi uniform pressure load.

11. The method of claim 9 wherein the acoustic load has a magnitude accounted for by mode-superposition.

12. The method of claim 9 wherein the acceleration load further comprises a 1 g negative base acceleration load.

13. The method of claim 9 wherein the acceleration load has a response generated by mode-acceleration.

* * * * *